(12) United States Patent
Ayliffe et al.

(10) Patent No.: US 7,515,268 B1
(45) Date of Patent: Apr. 7, 2009

(54) FLUORESCENCE-ACTIVATED CELL DETECTOR

(75) Inventors: Harold E. Ayliffe, Woodinville, WA (US); Curtis S. King, Kirkland, WA (US)

(73) Assignee: E.I. Spectra, LLC, Woodinville, WA (US)

( * ) Notice: Subject to any disclaimer, the term of this patent is extended or adjusted under 35 U.S.C. 154(b) by 161 days.

(21) Appl. No.: 11/701,711

(22) Filed: Feb. 2, 2007

Related U.S. Application Data

(60) Provisional application No. 60/764,697, filed on Feb. 2, 2006.

(51) Int. Cl.
*G01N 21/64* (2006.01)
(52) U.S. Cl. .............. 356/417; 356/246; 435/288.7; 436/172; 250/458.1; 250/461.2
(58) Field of Classification Search ............ 356/417
See application file for complete search history.

(56) References Cited

U.S. PATENT DOCUMENTS 3,910,702 A * 10/1975 Corll ................. 356/72

* cited by examiner

*Primary Examiner*—F. L Evans
(74) *Attorney, Agent, or Firm*—Brian C. Trask

(57) ABSTRACT

An apparatus, and method of use of such apparatus, for detecting particles of interest that are dispersed in a fluid mix, which typically includes other particles. The apparatus includes an interrogation platform arranged to operate in harmony with an opaque member having an orifice sized to promote single-file travel of the particles there-through. A radiation source is disposed on one side of the opaque member, and a radiation detector is disposed on the other side of the opaque member. Particles of interest are tagged using antibody-binding, fluorescing molecules. Radiation from the source causes the tagged particles to fluoresce in the vicinity of, and passing through, the orifice. The resulting fluorescence is detected by the radiation detector and indicates passage of the particles of interest. One workable opaque member is advantageously included in a thin film assembly carried on a removable and disposable card that is adapted for reception in the interrogation platform.

20 Claims, 10 Drawing Sheets

FLUORESCENCE-ACTIVATED CELL DETECTOR

RELATED APPLICATIONS

This application claims the benefit under 35 U.S.C. 119(e) of the filing date of Provisional Application Ser. No. 60/764, 697, filed Feb. 2, 2006, for "FLUORESCENCE-ACTIVATED CELL DETECTOR", the entire disclosure of which is hereby incorporated by reference as though set forth herein in its entirety.

BACKGROUND

1. Field of the Invention

This invention relates to optically-based evaluation of particles suspended in a fluid carrier medium. It is particularly directed to an improved apparatus and method for carrying out interrogation of particles by applying radiation to such particles and detecting a shift in wavelength of radiation emitted by selected ones of those particles.

2. State of the Art

Flow cytometry is a well established technique that is used to determine certain physical and chemical properties of microscopic particles by sensing certain optical properties of the particles. Many books and articles are available detailing aspects of this useful investigational tool. For example, operational principles of, and procedures for use of, modern cytometers are set forth in "Practical Flow Cytometry" by Howard M. Shapiro. Flow cytometry is currently used in a wide variety of applications including hematology, immunology, genetics, food science, pharmacology, microbiology, parasitology and oncology.

In flow cytometry, microscopic particles entrained in a carrier fluid are typically arranged in single-file inside a core stream using hydrodynamic focusing. The particles are then individually interrogated by an optical detection system. The interrogation typically includes directing a light beam from a radiation source, such as a laser, transversely across the focused stream of single-file particles. The light beam is scattered by each particle to produce a scatter profile. The scatter profile may be analyzed by measuring the light intensity at both small and larger scatter angles. Certain physical and/or chemical properties of each particle can then be determined from the scatter profile.

It is also known to apply fluorescing markers to selected particles of interest prior to processing such particles in a cytometer. For example, particles such as blood cells can be "tagged" with fluorescent molecules by using conjugated monoclonal antibodies. The wavelength of the radiation source (typically a laser), is matched to the excitation wavelength of the fluorescing molecule marker. The tagged particles fluoresce in the cytometer when excited by the transversely oriented laser beam. The fluorescence given off by the excited particle can be detected by an appropriately configured detector, which is conventionally mounted transverse to the path of the particles in the interrogation portion of the cytometer. Therefore, cells tagged with fluorescing markers can be easily detected for counting, or other data manipulation.

Unfortunately, flow cytometers are undesirably complex and expensive pieces of equipment. Care must be taken to ensure the machine is set up correctly, and properly calibrated. It would be an advance to provide a robust, inexpensive apparatus that can be used to promote single-file particle travel through an optically based interrogation zone to promote rapid processing of a plurality of different particle-bearing fluid samples.

BRIEF SUMMARY OF THE INVENTION

This invention provides an apparatus and method for optically-based evaluation of particles suspended in a fluid carrier medium. The apparatus includes an interrogation platform disposable in association with a plumbing arrangement adapted to transport particles suspended in a fluid. The plumbing arrangement is structured to urge transit of particles carried in a fluid in substantially single-file through a first orifice disposed to provide a first flow path through a substantially opaque member. Prior to interrogation, the particles of interest are generally tagged with a fluorescing marker of some sort.

A radiation source is disposed on a first side of the opaque member. An operable radiation source is arranged to apply primary radiation in a direction along a radiation vector into a zone associated with the first orifice effective to excite a first subset of particles passing through the zone operably to cause an emission of fluorescence from a first particle selected from the first subset. A first portion of fluorescence from the excited particle is then directed for transmission in a direction from the first side toward a second side of the substantially opaque member and through the first orifice. A radiation detector is disposed on the second side of the substantially opaque member. The radiation detector is operably arranged for reception and detecting of the fluorescence from the excited particle.

Desirably, the primary radiation has a first characteristic wavelength, and the fluorescence has a second characteristic wavelength that is different from the first characteristic wavelength, known as a Stokes shift. Certain embodiments include a first filter disposed between the radiation source and radiation detector. In such case, the first filter is typically configured and arranged to resist reception of primary radiation by the radiation detector. Sometimes, a second filter may be disposed on the first side of the opaque member. Such second filter would generally be configured and arranged to resist transmission there-through of radiation departing from the first characteristic wavelength. Certain embodiments may also include a collecting lens disposed on the second side of the opaque member. If present, a collecting lens is typically configured and arranged to urge part of the fluorescence toward a detecting element of the radiation detector. A workable collecting lens may include a fiber optic cable, or a convex focusing lens.

In certain preferred embodiments, the radiation vector from the radiation source is oriented at an acute angle to a through-axis of the first orifice. It is currently preferred for such acute angle to be between about 15 degrees and about 75 degrees. The goal of applying the primary radiation vector at an acute angle is simply to avoid direct reception of such radiation by the detector. In other words, it is currently preferred to make substantially the entire detected signal available for signal processing (e.g. to make better use of the gain in the detector).

A plumbing arrangement operable in an alternative embodiment constructed according to certain principles of the instant invention is configured to urge transit of particles in substantially single-file through a plurality of orifices. Each such orifice is disposed to provide a respective flow path through the substantially opaque member. A radiation source is arranged to apply primary radiation into a zone associated with the plurality of orifices effective to excite a first subset of_ particles passing through the zone operably to cause an emission of fluorescence from certain particles selected from the first subset, with fluorescence from certain tagged particles being directed for transmission in a direction from the first side toward a second side of the substantially opaque member. The radiation detector is operably arranged on the opposite side of the opaque member for reception and detecting of any resulting fluorescence.

A currently preferred plumbing arrangement comprises structure arranged such that fluid flow through the first orifice is directed approximately orthogonal to fluid flow in a channel disposed immediately downstream of the first orifice. Further, fluid flow through the first orifice is desirably directed approximately orthogonal to fluid flow in a channel disposed immediately upstream of the first orifice. One representative first orifice has a characteristic dimension sized between about 5 microns and about 200 microns. A thickness of the opaque member of a currently preferred embodiment is between about 10 microns and about 300 microns. One operable opaque member includes a membrane carrying an opaque substance as a first coating disposed on one side thereof. Sometimes, a second opaque layer may also be included as a second coating disposed on a side opposite the one side. The opaque member can also be formed from a substance that is inherently non-transmitting of radiation. In any case, when the plumbing arrangement is carried on a removable cartridge, a radiation transmission window is formed through the thickness of the cartridge.

One operable method of using the instant apparatus includes preparing a sample of particles suspended in a fluid carrier medium by mixing a quantity of particles with antibody-bound fluorescently labeled molecules. The sample is then incubated for a period of time sufficient to permit antibody-bound fluorescently labeled molecules to bind to particles of interest in the sample. An interrogation platform is provided to interrogate the sample. A currently preferred platform is configured to operate on a detection zone disposed in association with an orifice configured to provide a flow path through a substantially opaque member. The orifice is sized sufficiently in agreement with a characteristic size of the particles of interest as to promote substantially single-file travel of such particles of interest there-through. The interrogation platform further includes a radiation source disposed on one side of the substantially opaque member and a radiation detector disposed on an opposite side of the substantially opaque member. A portion of the sample is then caused to flow through the detection zone. The source of radiation is used to impinge primary radiation, having a first characteristic wavelength, into the detection zone operably to excite antibody-bound fluorescently labeled molecules to promote emission there-from of secondary radiation having a second characteristic wavelength. The radiation detector is used to detect the secondary radiation. Subsequent to interrogation, the portion of the sample flows away from the detection zone.

In one sample preparation procedure, incubation occurs at a temperature between about 20 degrees Celsius and about 39 degrees Celsius. In a currently preferred apparatus and method, the opaque member is included in a plumbing arrangement comprising a thin film assembly carried on a removable card. Such plumbing arrangement causes fluid flow away from the detection zone to occur in an essentially orthogonal direction compared to fluid flow through said orifice. Also, the removable card is desirably configured and arranged to interface with structure of the interrogation platform to hold the card in position during an interrogation procedure. Therefore, the method can also include inserting such removable card into operable position in association with the interrogation platform.

BRIEF DESCRIPTION OF THE DRAWINGS

In the drawings, which illustrate what are currently considered to be the best modes for carrying out the invention.

DETAILED DESCRIPTION OF THE ILLUSTRATED EMBODIMENTS

Reference will now be made to the drawings in which the various elements of the illustrated embodiments will be given numerical designations and in which the invention will be discussed so as to enable one skilled in the art to make and use the invention. It is to be understood that the following description is only exemplary of the principles of the present invention, and should not be viewed as narrowing the claims which follow.

Figure 1:
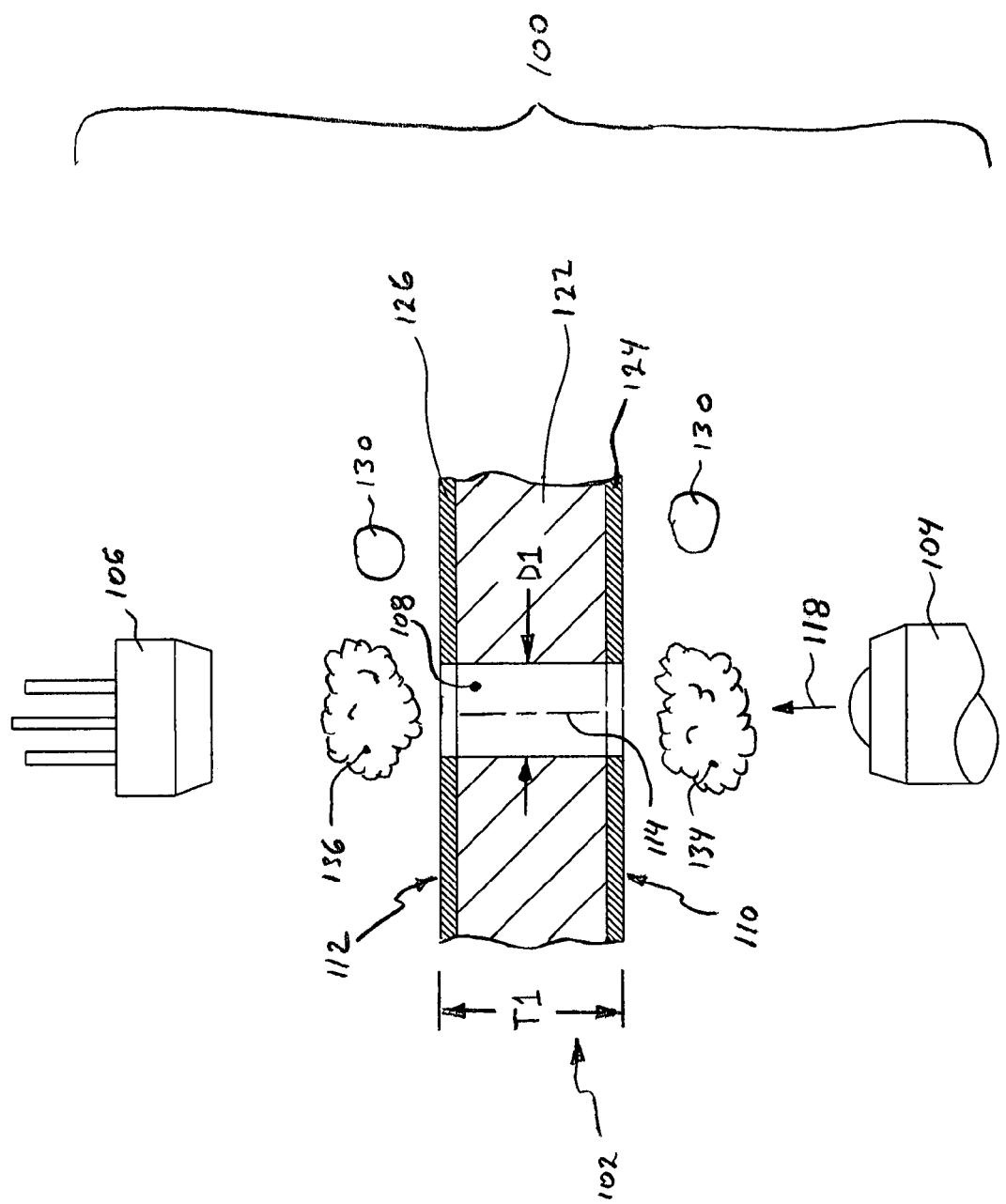
FIG. 1 is a schematic of a cross-section taken through a first embodiment illustrating general principles of operation of the invention.

A schematic illustrating a generalized operable arrangement of structure employed in embodiments of the invention is indicated generally at 100 in FIG. 1. As illustrated, embodiment 100 includes an opaque member, generally indicated at 102, disposed between a radiation source 104 and a radiation detector 106. At least one orifice 108 is disposed in opaque member 102 to provide a flow path between a first side, generally indicated at 110, and a second side, generally indicated at 112. Orifice 108 may be characterized as having a through-axis 114 extending between the first and second sides 110 and 112 of opaque member 102, respectively.

The thickness, T1, of an opaque member and characteristic size, D1, of an orifice are typically sized in agreement with a size of a particle of interest to promote single-file travel of the particle through the opaque member, and to have only one particle inside the orifice at a time. In the case where the apparatus is used to interrogate blood cells, the thickness of the opaque member may typically range between about 10 microns and about 300 microns, with a thickness of about 50 microns being currently preferred. The diameter, or other characteristic size of the orifice, may range between about 5 and 200 microns, with a diameter of about 100 microns being currently preferred.

An operable opaque member 102 functions, in part, to reduce the quantity of primary radiation 118 that is emitted by source 104, which is received and detected by radiation detector 106. Primary radiation 118 is illustrated as a vector having a direction. Desirably, substantially all of the primary radiation 118 is prevented from being detected by the radiation detector 106. In any case, operable embodiments are structured to resist saturation of the detector 106 by primary radiation 118. As illustrated in the arrangement depicted in FIG. 1, primary radiation 118 may simply pass through orifice 108 for reception by the radiation detector 106. Therefore, as will be further detailed below, certain embodiments may employ one or more selective radiation filters as a measure to control radiation received by detector 106.

The opaque member 102 illustrated in FIG. 1 includes a core element 122, carrying a first coating 124 disposed on first side 110, and a second coating 126 disposed on second side 112. A workable core 122 for use in detecting small sized particles can be formed from a thin polymer film, such as PET having a thickness of about 0.005 inches. Such polymer material is substantially permeable to radiation, so one or more coatings, such as either or both of coating 124 and 126, is typically applied to such core material. A workable coating includes a metal or alloy of metals that can be applied as a thin layer, such as by sputtering, vapor deposition, or other well-known technique. Ideally, the metal layer should be about 2-times as thick as the wavelength of the primary radiation, e.g. about 1 µm in one operable embodiment. The resulting metallized film may be essentially impervious to transmission of radiation, except where interrupted by an orifice. Aluminum is one metal suitable for application on a core 122 as a coating 124 and/or 126. Of course, it is also within contemplation to alternatively use a bare core element that is, itself, inherently resistant to transmission of radiation.

The apparatus 100 is configured to urge a plurality of particles 130 in substantially single-file through orifice 108. A particle 130 typically passes through an excitation zone as the particle approaches, passes through, and departs from the orifice 108. Of note, the direction of particle-bearing fluid flow may be in either direction through orifice 108. An excitation zone typically includes the through-channel defined by orifice 108. An excitation zone may also include a volume indicated by lower cloud 134, which encompasses a volume in which a particle may reside and be in contact with primary radiation. An excitation zone may further include a volume indicated by upper cloud 136, which also encompasses a volume in which a particle may reside and be in contact with primary radiation.

In certain cases, e.g. where there may be a plurality of orifices, the term "zone" may include a plurality of such distributed zones. However, the appropriate meaning of the term "zone" is believed to be aduceable in context. In the excitation zone, primary radiation 108 causes certain particles to fluoresce, thereby emitting radiation at a different wavelength compared to the primary radiation 108 and in substantially all three-dimensions. The fluorescence radiation emitted by those certain particles is then detected by the radiation detector 106.

Figure 11:
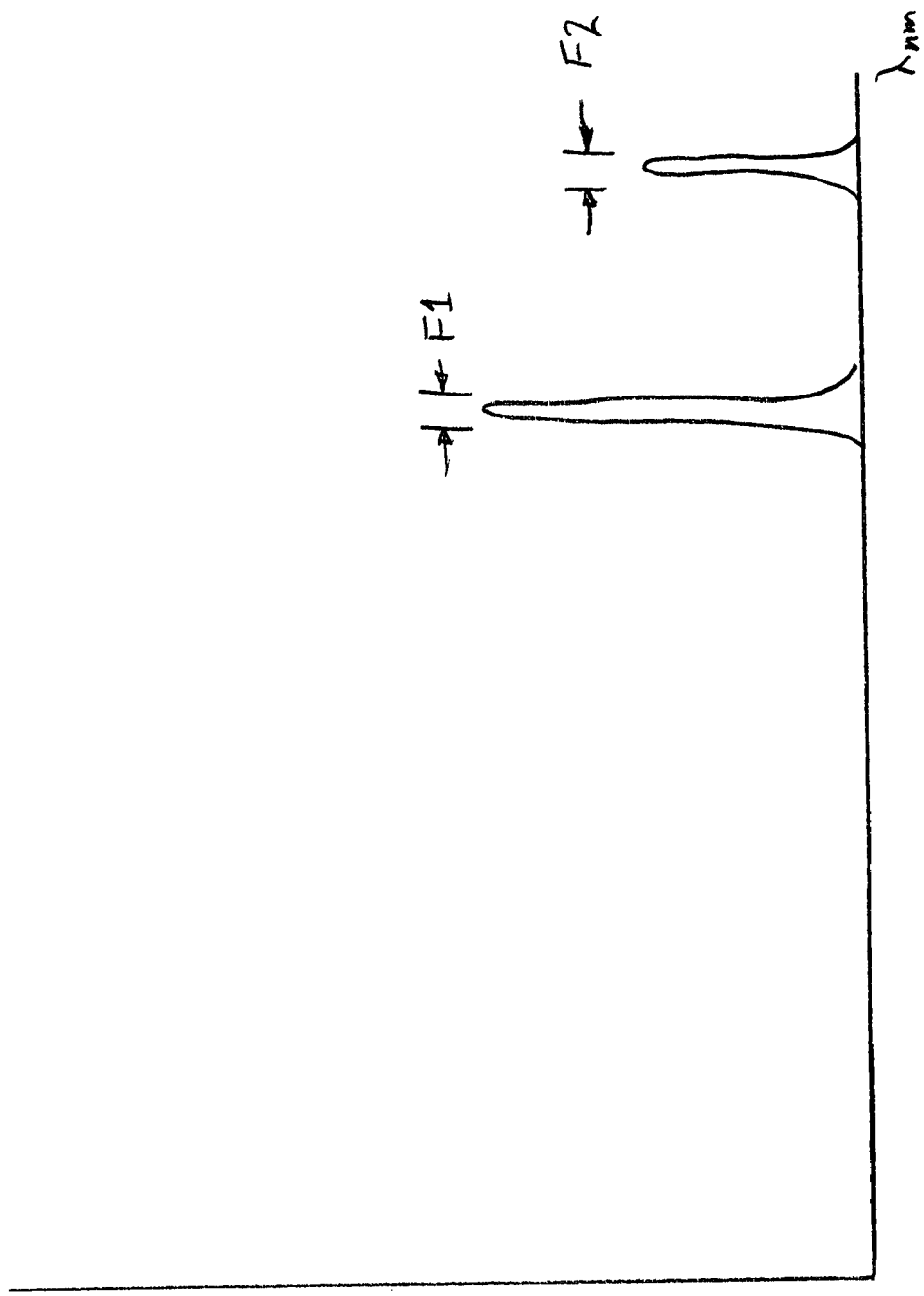
FIG. 11 is a plot illustrating characteristic wavelengths for a representative primary radiation and a resulting fluorescent response.

It should be noted, for purpose of this disclosure, that the term "wavelength" is typically employed not with reference only to a single specific wavelength, but rather to encompass a spread of wavelengths grouped about a characteristic, or representative, wavelength. With reference to FIG. 11, the characteristic wavelength F1 (e.g. excitation wavelength) of the primary radiation 118 is sufficiently different from the characteristic wavelength F2 of the fluorescence (e.g. emission wavelength) to enable differentiation between the two. Furthermore, the difference between such characteristic wavelengths, or Stokes shift, is desirably sufficiently different to enable, in certain embodiments, including a selective-pass filter element between the radiation source 104 and detector 106 effective to block transmission of primary radiation toward the detector, while permitting transmission of the fluorescence through the selective-pass filter to the detector.

With reference again to FIG. 1, the embodiment 100 may essentially be disposed in a suitably sized container that is divided into two portions by the opaque member. Flow of fluid (and particles entrained in that fluid) through the orifice 108 could be controlled by a difference in pressure between the two divided portions. However, it is typically desired to provide more control over the flow path of particles in the vicinity of the orifice 108 than such an embodiment would permit. For example, a clump of particles disposed near an entrance or exit of the orifice 108 could shield a particle of interest from the primary radiation 118 to the extent that fluorescence does not occur, thereby causing a miscount, or preventing detection of such a shielded particle of interest.

Figure 2:
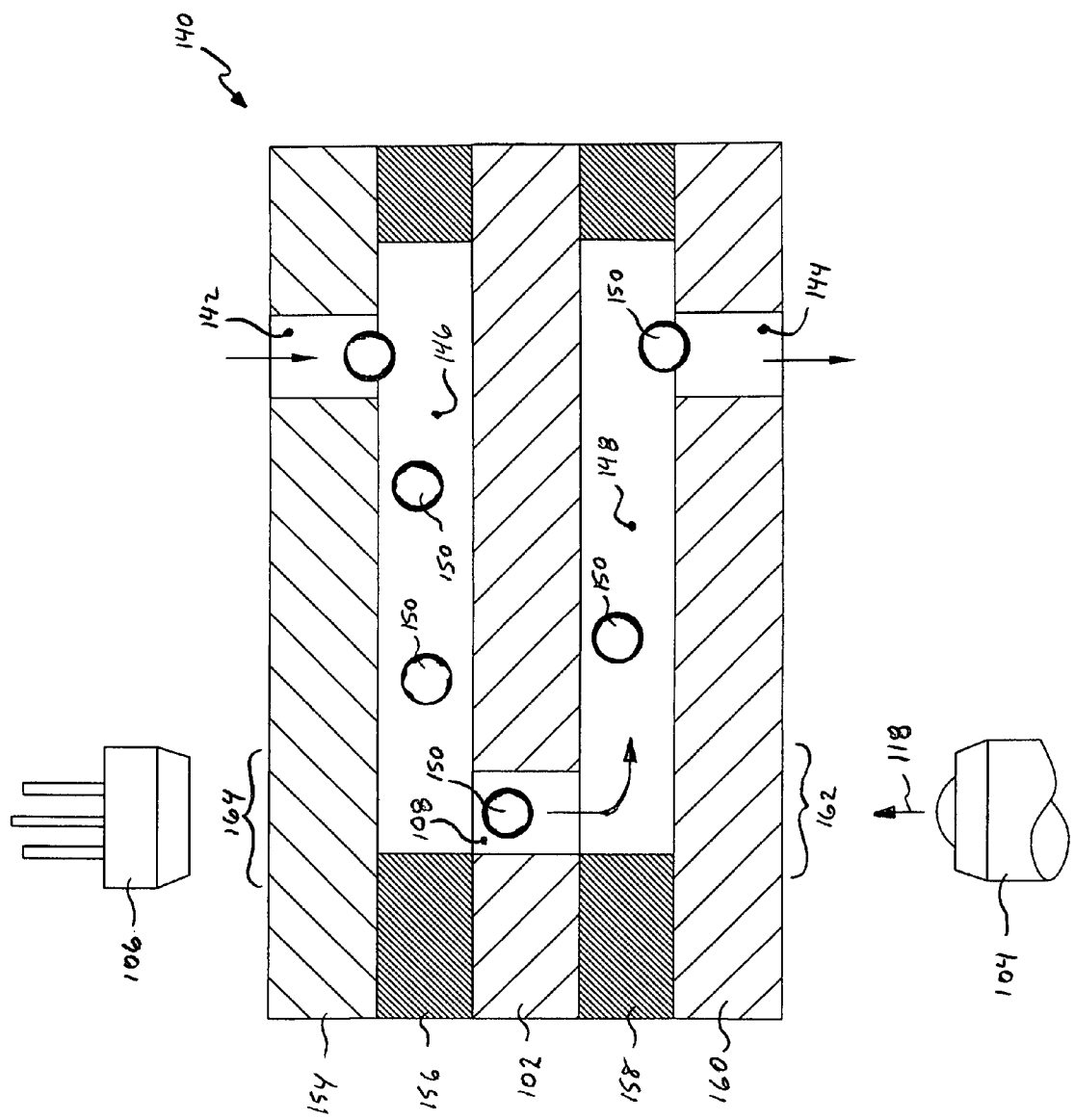
FIG. 2 is a cross-section in elevation illustrating certain details of a workable plumbing arrangement that may be associated with certain structure of an interrogation platform.

The multi-layered embodiment, generally indicated at 140 and illustrated in FIG. 2, provides a plumbing arrangement that is structured to resist particle clumping near the orifice 108, and consequential lack of detection of a particle of interest. Multilayer assembly 140 is structured to urge fluid flow through the orifice 108 in a direction that is essentially orthogonal to fluid flow in channel portions adjacent to, and upstream and downstream of, the orifice 102. Such fluid flow resists stacking of particles in a thickness direction of the plumbing arrangement 140, and thereby reduces likelihood of undetected particles of interest.

Plumbing arrangement 140 includes five layers configured and arranged to form a channel system effective to direct flow of particle bearing fluid from a supply chamber 142, through orifice 108 in an opaque member 102, and toward a waste chamber 144. Desirably, a depth of fluid guiding channels 146 and 148 are sized in general agreement with a size of a particle 150, to resist "stacking" particles near the orifice 108. Fluid can be moved about on the device 140 by imposing a difference in pressure between chambers 142 and 144, or across orifice 108 disposed in opaque member 102. For example, a positive pressure may be applied to the supply chamber 142. Alternatively, a negative pressure may be applied to the waste chamber 144. Both positive and negative pressures may be applied, in certain cases. Alternative fluid motive elements, such as one or more pumps, may be employed to control particle travel through opaque member 102.

Although both of supply chamber 142 and waste chamber 144 are illustrated as being open, it is within contemplation for one or both to be arranged to substantially contain the fluid sample within a plumbing device that includes a multilayer element 104. Also of note, although a top-down fluid flow is illustrated in FIG. 2, fluid flow may be established in either direction through orifice 108. In one reverse-flow configuration, the positions of supply chamber 142 and waste chamber 144 would simply be reversed from their illustrated positions. In an alternative reverse-flow arrangement, the positions of the radiation source 104 and detector 106 would be reversed from their illustrated positions.

Figure 3:
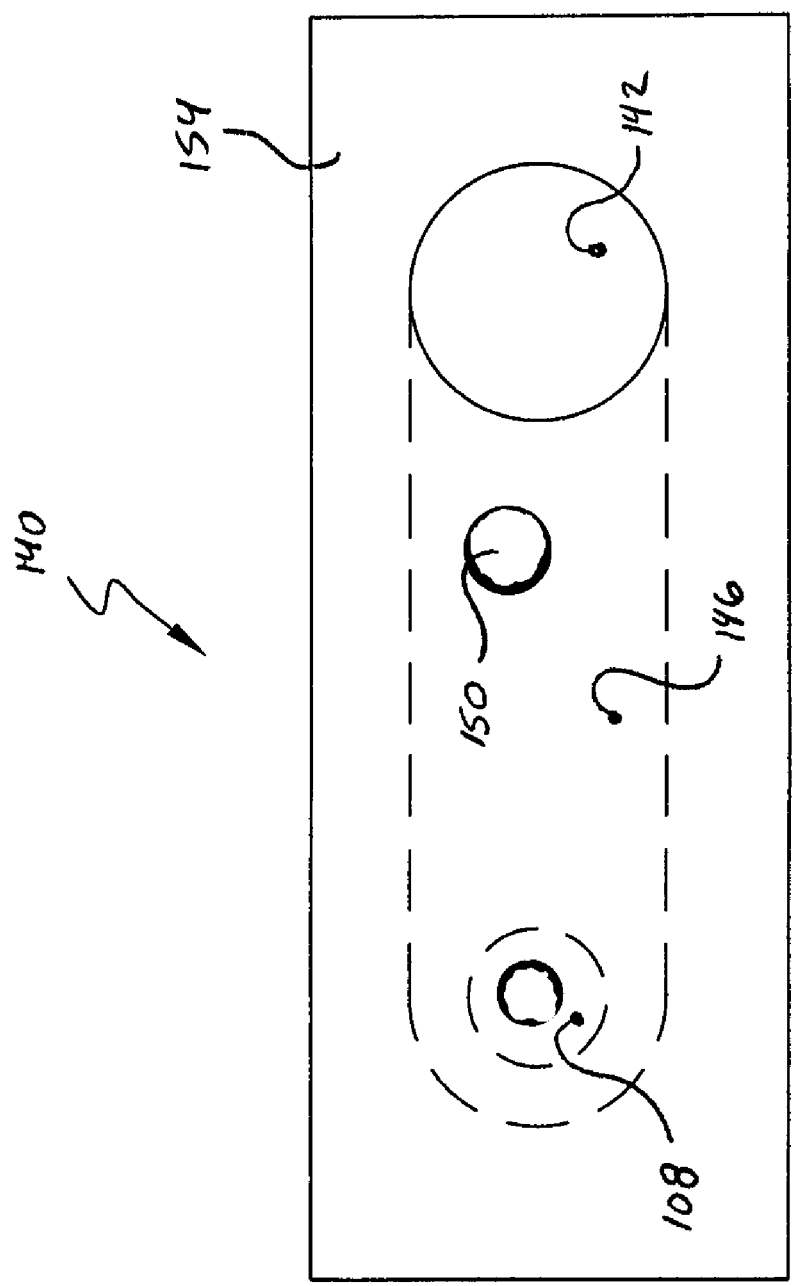
FIG. 3 is a top view of the plumbing arrangement illustrated in FIG. 2.

The multilayer plumbing arrangement 140 illustrated in FIGS. 2 and 3 includes a top cap layer 154, a top channel layer 156, an opaque member 102, a bottom channel layer 158, and a bottom cap layer 160. Such layers can be stamped, e.g. die cut, or manufactured by using a laser or water jet, or other machining technique, such as micro machining, etching, and the like. In a currently preferred embodiment 140 that is used to interrogate blood cells, the various layers are typically made from thin polymer films, which are then bonded together to form the multilayer assembly. Desirably, the thickness of at least the channel layers 156, 158 are on the order of the characteristic size of particles of interest to promote single-file travel of particles through an interrogation zone. A workable thickness of such layers in currently preferred devices used to interrogate blood cells typically ranges between about 10 microns and about 300 microns.

In any case, at least a portion of bottom layer 160 is adapted to form a bottom window 162, through which radiation 118 may be transmitted into an excitation zone. Similarly, top layer 154 includes a portion forming a window 164, through which fluorescence may be transmitted. Therefore, the assembly 140 is arranged to form a window permitting radiation to pass through its thickness. Such window includes window portions 162, 164, certain portions of channels 146 and 148 disposed in the vicinity of orifice 108, and the orifice 108 itself. Radiation can therefore be directed through the thickness of the assembly 140 in the vicinity of the orifice 108.

Figure 4:
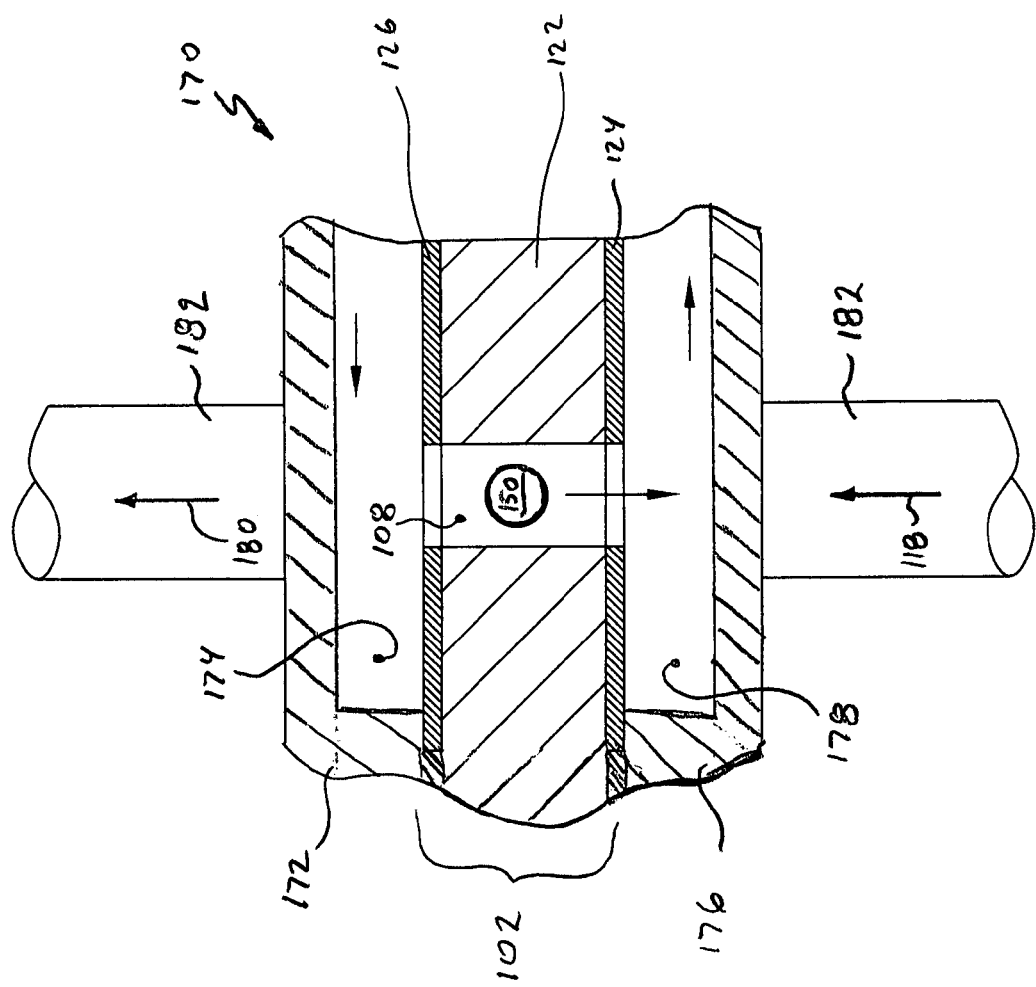
FIG. 4 is a cross-section in elevation illustrating certain details of another workable plumbing arrangement associated with certain structure of an interrogation platform.

The plumbing arrangement illustrated in FIG. 4, and generally indicated at 170, includes a top layer 172, which carries a carved-out fluid-flow channel 174. Bottom cap layer 176 similarly includes a carved-out channel 178. Opaque member 102 is adapted to dispose orifice 108 for fluid communication between channels 174 and 178. Bottom layer 176 is formed from a material that permits transmission of radiation in an appropriate spectrum to enable excitation of particles, which pass through an excitation zone associated with the orifice 108, by primary radiation 118. Top layer 172 is formed from a material that permits transmission of radiation in an appropriate spectrum to enable transmission of fluorescence 180 toward a radiation detector. Top layer 172 may also be adapted to resist transmission of primary radiation 118. Again, the fluid and particle flow may be in a direction reversed from that illustrated. As illustrated in FIG. 4, sometimes a plumbing arrangement, such as arrangement 170, may be coupled to, or associated with, a radiation source and/or a radiation detector by way of a fiber optic cable 182. A fiber optic cable 182 may be disposed to operate as a lens effective to capture a substantial portion of fluorescence transmitted through the plumbing arrangement 170.

Figure 5:
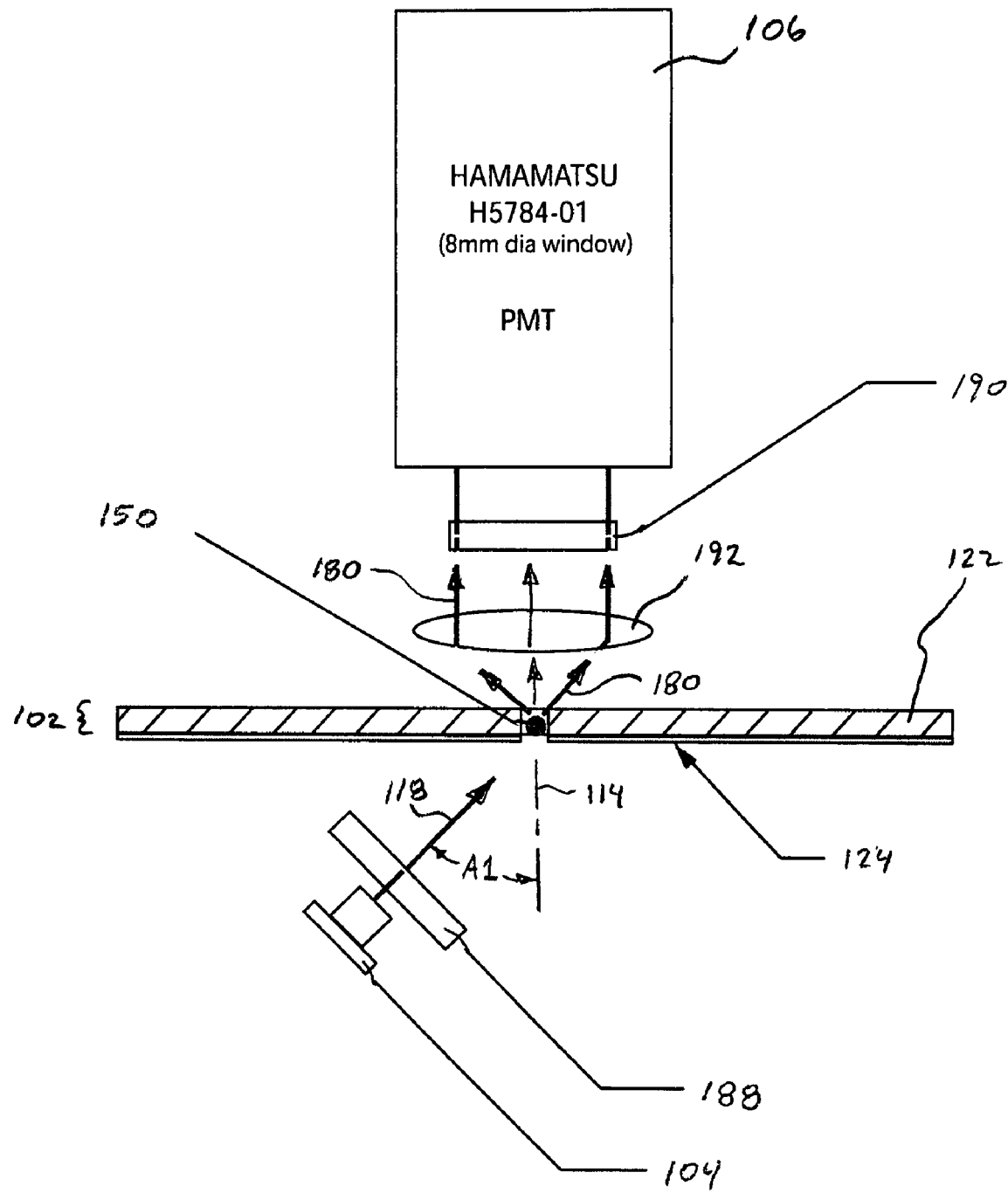
FIG. 5 is a view in elevation of a currently preferred arrangement for certain structure of an operable interrogation platform.

Because fluorescence propagates from a tagged and excited particle of interest in substantially all directions, the primary radiation may be directed to an excitation zone from a side, instead of only from directly below such zone. With reference now to FIG. 5, sometimes it is preferred to apply primary radiation 118 at an acute angle A1 to axis 114 of orifice 108. In such case, the opaque member 102 may even function substantially as an operable filter to resist direct transmission of primary radiation 118 to a radiation detector. As illustrated, radiation vector 118 can be oriented to pass through, or partially into, orifice 108 without being detected by radiation detector 106. However, when a tagged particle 150 is present in an excitation zone (such as orifice 108 as illustrated), the resulting fluorescence 180 may still be detected by the radiation detector 106. While a workable angle A1 may be between 0 and 90 degrees, it is currently preferred for angle A1 to be between about 15 and about 75 degrees.

A radiation source 104 may be formed from a broad spectrum radiation emitter, such as a white light source. In such case, it is typically preferred to include a pre-filter 188 adapted to pass, or transmit, radiation only in a relatively narrow band encompassing the characteristic value required to excite a particular fluorescing agent associated with a particle of interest. It is generally a good idea to limit the quantity of applied radiation 118 that is outside the excitation wavelength to reduce likelihood of undesired saturation of the radiation detector, and consequent inability to detect particles of interest.

It is currently preferred to use a red diode laser, and to include a short pass filter (after the diode laser) that passes primary light radiation with wavelengths shorter than 640 nm. It is also currently preferred to include a band pass filter (prior to the photodetector) with a peak that matches a particular selected fluorescence peak. Commercially available dyes may be obtained having characteristic fluorescent peaks at 660, 694, 725, and 775 nanometers.

With continued reference to FIG. 5, sometimes it is preferred to include a post filter 190 that resists transmission of radiation outside the characteristic wavelength of the fluorescence 180. Such an arrangement helps to avoid false readings indicative of presence of a particle of interest in an excitation zone. Also, to assist in obtaining a strong signal, an optical enhancement, such as a lens 192, can be included to gather fluorescence 180 and direct such radiation toward the radiation detector 106. Illustrated lens 192 may be characterized as a convex focusing lens, and typically is disposed to focus on a point located inside the orifice 108.

Figure 6:
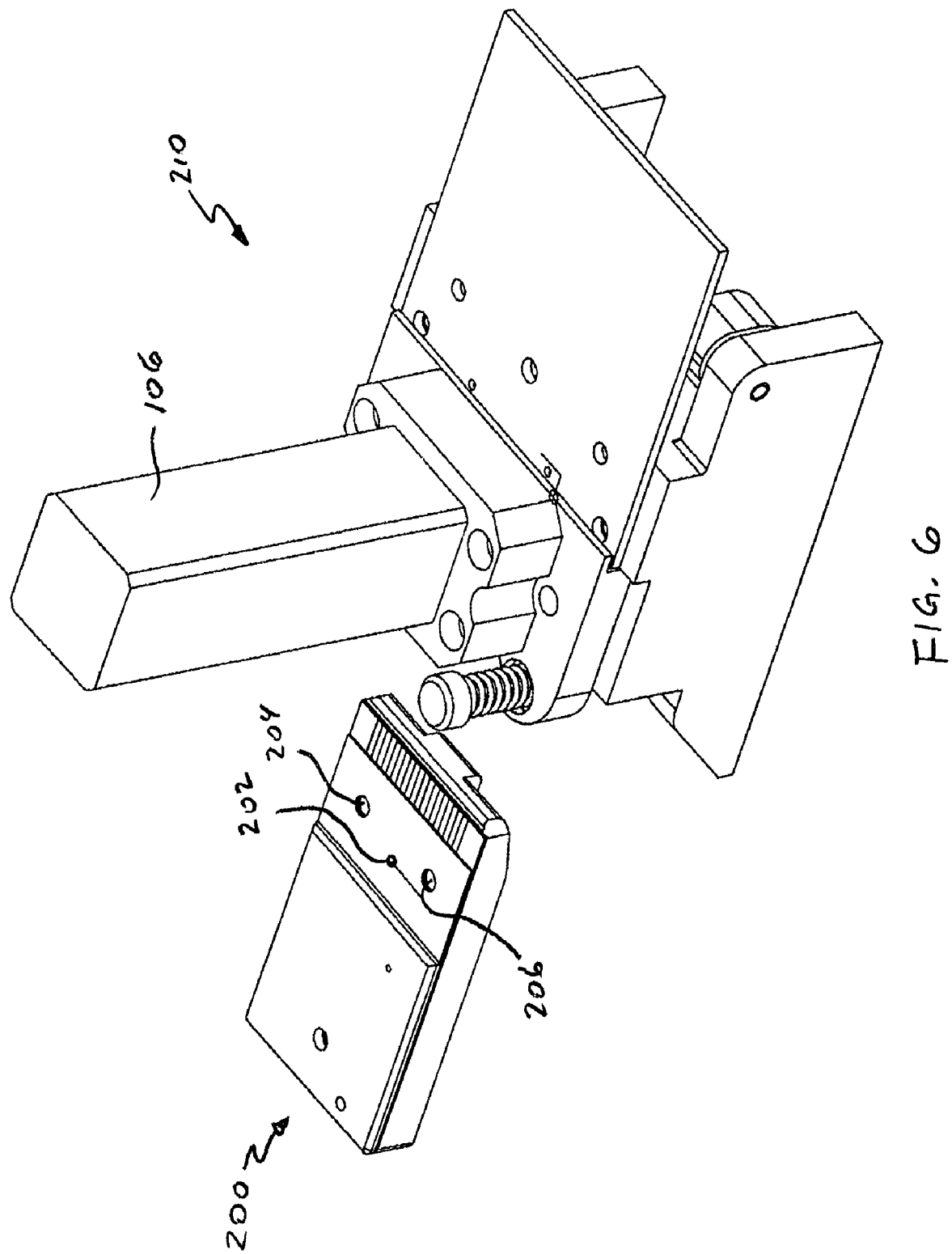
FIG. 6 is a perspective view from above of a workable interrogation platform and a removable cartridge carrying a plumbing arrangement.

With reference to FIG. 6, a plumbing arrangement, such as 140, 170, may be associated with a housing to form a cartridge assembly, generally indicated at 200. The cartridge may be configured to provide access through a radiation transmitting window 202 for purpose of exciting and detecting radiation. One or more fluid access ports 204, 206 may be provided to install a fluid sample into the cartridge 200, and to provide control over fluid motion through the cartridge 200. Such cartridge 200 can be configured to interface with holding structure of an interrogation platform, such as the interrogation platform generally indicated at 210, to associate the plumbing arrangement with the interrogation platform.

Figure 7:
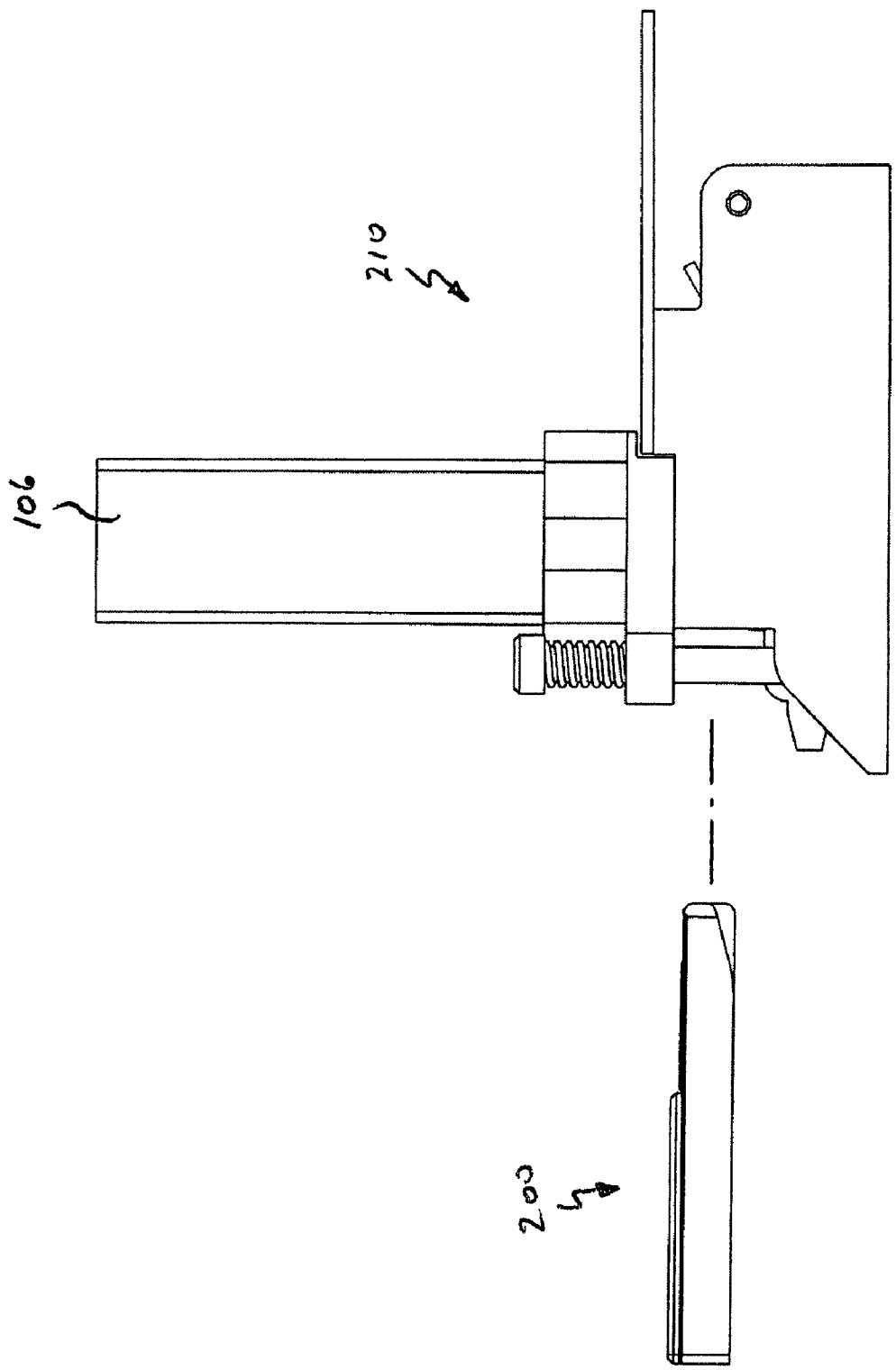
FIG. 7 is a side view in elevation of the structure illustrated in FIG. 6.
Figure 8:
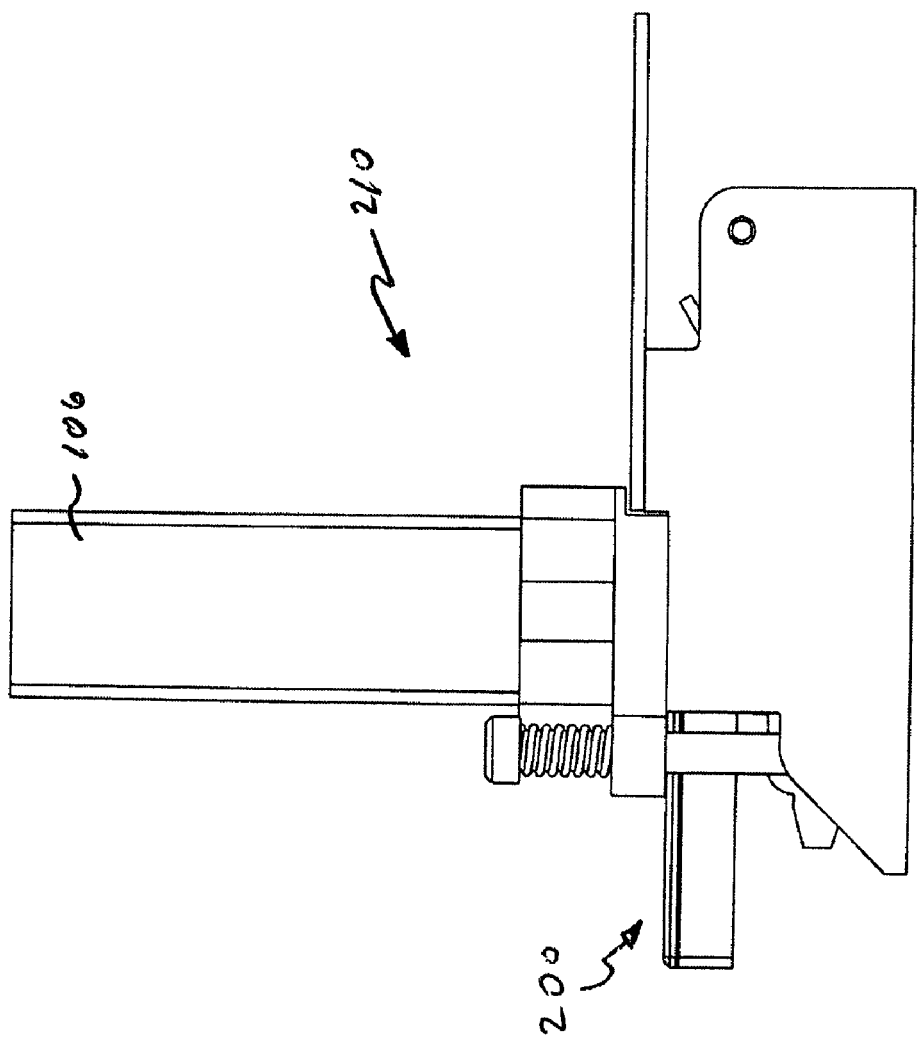
FIG. 8 is a side view in elevation of the structure illustrated in FIG. 6, with the cartridge seated in the interrogation platform.
Figure 9:
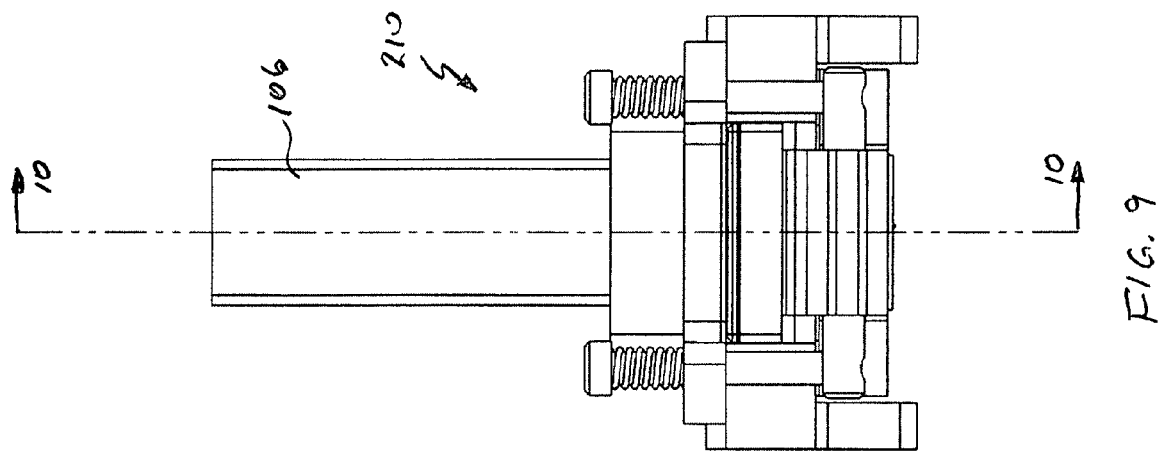
FIG. 9 is an end view in elevation of the structure illustrated in FIG. 6.
Figure 10:
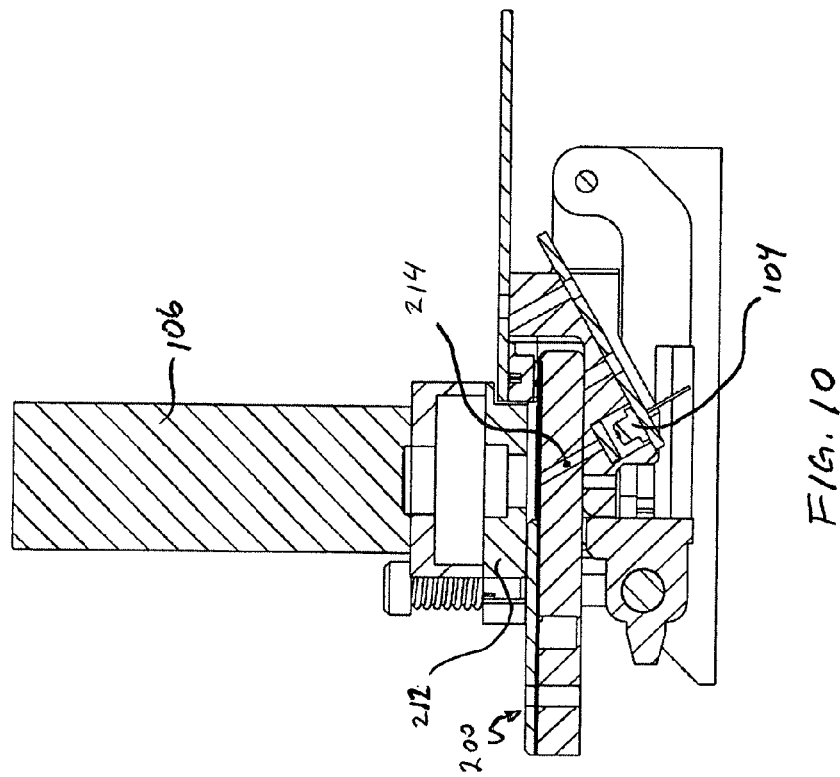
FIG. 10 is a cross-section view taken through section 10-10 in FIG. 9, and looking in the direction of the arrows.

FIG. 7 illustrates a cartridge 200 in position to slide into reception in holding structure of the platform 210. FIG. 8 illustrates cartridge 200 in an installed position in holding structure of the platform 210, and ready to perform an interrogation of particles of interest. FIGS. 9 and 10 cooperatively show details of a currently preferred platform 210. Cartridge 210 may be held in a test position by retaining structure, such as illustrated spring-loaded platen 212. The source of primary radiation 104 is disposed to emit primary radiation through tunnel 214 operably to radiate particles in an excitation zone of an associated plumbing arrangement. Radiation detector 106 is disposed to detect any resulting fluorescence.

Certain components that are operable to construct an apparatus according to certain principles of the instant invention are commercially available. For example, one operable source of radiation 104 includes a red diode laser available under part number VPSL-0639-035-x-5-B, from Blue Sky Research, having a place of business located at 1537 Centre Point Drive, Milpitas, Calif. 95035. Filter elements 188, 190 are avilable from Omega Optical, having a place of business located at 21 Omega Dr., Delta Campus, Brattleboro, Vt. 05301. Preferred filters include part numbers, 660NB5 (Bandpass filter), and 640ASP (shortpass filter). An operable radiation detector includes a photomultiplier tube available from the Hamamatsu Corporation, having a place of business located at 360 Foothill Rd., Bridgewater, N.J. 08807, under part number H5784-01. Molecular Probes (a division of Invitrogen Corporation, www.probes.invitrogen.com) supplies a plurality dyes that are suitable for use in tagging certain particles of interest for interrogation using embodiments structured according to the instant invention. In particular, AlexaFluor 647, AlexaFluor 700, and APC-AlexaFluor 750 find application to interrogation of blood cells. These dyes are also commonly used in flow cytometric applications and have specific excitation and emission characteristics. Each dye can be easily conjugated to antibodies for labeling, or tagging, different cell types.

In one method for using the invention, particles (e.g. blood cells) of interest are mixed with a commercially available (i.e., obtained from Invitrogen Corporation, Carlsbad, Calif.) or custom manufactured antibody-bound fluorescently labeled molecules. The mixture is then incubated for a brief period of time (approximately 5 to 15 minutes) at a temperature typically between about room temperature and abut 39 degrees Celsius. For preparation of white blood cells for interrogation, a small amount of fluorescent dye (e.g. 10 microliters) is added to about 10 microliters of whole blood, vortexed and then incubated for about 15 minutes at room temperature in the dark. A lysing agent is then added to lyse the red blood cells. Once added, the mixture is again vortexed and then allowed to incubate for another 15 minutes (in the dark).

Fluorescent markers bind to cells (or other particles of interest) in the sample during the incubation period. The particles suspended in solution are then passed through the orifice detection zone from one (supply) reservoir to another (waste) reservoir, typically by applying either an external vacuum source to pull the sample through or an external positive gas source to push the sample through. Fluorescently labeled particles are excited with primary radiation (light) as they traverse the opaque member (through the orifice) which causes fluorescence and subsequent emission of light having a secondary wavelength (which is released into the opposite or detector side of the opaque member). Particles flow away from the detection orifice to a waste reservoir or storage containment area.

While the invention has been described in particular with reference to certain illustrated embodiments, such is not intended to limit the scope of the invention. The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An apparatus, comprising:
an interrogation platform disposable in association with a plumbing arrangement adapted to transport particles suspended in a fluid, said plumbing arrangement being configured to urge transit of said particles in substantially single-file through a first orifice disposed to provide a first flow path through a substantially opaque member;
a radiation source disposed on a first side of said opaque member, said radiation source being arranged to apply primary radiation in a direction along a radiation vector into a zone associated with said first orifice effective to excite a first subset of particles passing through said zone operably to cause an emission of fluorescence from a first particle selected from said first subset, with a first portion of fluorescence from said first particle being directed for transmission in a direction from said first side toward a second side of said substantially opaque member and through said first orifice; and
a radiation detector disposed on said second side of said substantially opaque member, said second side being opposite said first side, said radiation detector being operably arranged for reception and detecting of said first portion.

2. The apparatus according to claim 1, wherein:
said primary radiation has a first characteristic wavelength; and
said fluorescence has a second characteristic wavelength that is different from said first characteristic wavelength.

3. The apparatus according to claim 2, further comprising:
a first filter disposed between said radiation source and said radiation detector, said first filter being configured and arranged to resist reception of said primary radiation by said radiation detector.

4. The apparatus according to claim 3, further comprising:
a second filter disposed on said first side, said second filter being configured and arranged to resist transmission there-through of radiation departing from said first characteristic wavelength.

5. The apparatus according to claim 1, further comprising:
a collecting lens disposed on said second side, said collecting lens being configured and arranged to urge part of said first portion toward a detecting element of said radiation detector.

6. The apparatus according to claim 5, wherein:
said collecting lens comprises a fiber optic cable.

7. The apparatus according to claim 5, wherein:
said collecting lens comprises a convex focusing lens.

8. The apparatus according to claim 1, wherein:
said radiation vector is oriented at an acute angle to a through-axis of said first orifice.

9. The apparatus according to claim 8, wherein:
said acute angle is between about 15 degrees and about 75 degrees.

10. The apparatus according to claim 1, wherein:
said plumbing arrangement is configured to urge transit of said particles in substantially single-file through a plurality of orifices, each such orifice being disposed to provide a respective flow path through said substantially opaque member;
said radiation source is arranged to apply primary radiation into a zone associated with said plurality of orifices effective to excite a first subset of particles passing through said zone operably to cause an emission of fluorescence from certain particles selected from said first subset, with fluorescence from said certain particles being directed for transmission in a direction from said first side toward a second side of said substantially opaque member; and
said radiation detector is operably arranged for reception and detecting of said fluorescence.

11. The apparatus according to claim 1, wherein said plumbing arrangement comprises structure arranged such that:
fluid flow through said first orifice is directed approximately orthogonal to fluid flow in a channel disposed immediately downstream of said first orifice.

12. The apparatus according to claim 1, wherein said plumbing arrangement comprises structure arranged such that:
fluid flow through said first orifice is directed approximately orthogonal to fluid flow in a channel disposed immediately upstream of said first orifice.

13. The apparatus according to claim 1, wherein:
said first orifice has a characteristic dimension sized between about 5 microns and about 200 microns.

14. The apparatus according to claim 1, wherein:
a thickness of said opaque member is between about 10 microns and about 300 microns.

15. The apparatus according to claim 1, wherein:
said opaque member comprises a membrane carrying an opaque substance as a first coating disposed on one side thereof.

16. The apparatus according to claim 15, further comprising:
a second opaque layer as a second coating disposed on a side opposite said one side.

17. The apparatus according to claim 15, further comprising:
a transmission window formed through the thickness of a removable cartridge, said cartridge being adapted to interface with structure of said interrogation platform, and carrying structure adapted to form said plumbing arrangement.

18. A method for detecting particles of interest, comprising the steps of:
a) preparing a sample of particles suspended in a fluid carrier medium by mixing a quantity of said particles with antibody-bound fluorescently labeled molecules;
b) incubating said sample for a period of time sufficient to permit said antibody-bound fluorescently labeled molecules to bind to said particles of interest in said sample;
c) providing an interrogation platform configured to operate on a detection zone disposed in association with an orifice configured to provide a flow path through a substantially opaque member, said orifice being sized sufficiently in agreement with a characteristic size of said particles of interest as to promote substantially single-file travel of said particles of interest there-through, said interrogation platform further comprising a radiation source disposed on one side of said substantially opaque member and a radiation detector disposed on an opposite side of said substantially opaque member;
d) causing a portion of said sample to flow through said detection zone;
e) using said source of radiation to impinge primary radiation, having a first characteristic wavelength, into said detection zone operably to excite said antibody-bound fluorescently labeled molecules to promote emission there-from of secondary radiation, said secondary radiation having a second characteristic wavelength;
f) using said radiation detector to detect said secondary radiation; and
g) causing said portion of said sample to flow away from said detection zone.

19. The method according to claim 18, wherein:
the incubation of step b) occurs at a temperature between about 20 degrees Celsius and about 39 degrees Celsius.

20. The method according to claim 18, wherein:
said opaque member is included in a plumbing arrangement comprising a thin film assembly carried on a removable card, said plumbing arrangement causing fluid flow away from said detection zone to occur in an essentially orthogonal direction compared to fluid flow through said orifice, said removable card being configured and arranged to interface with structure of said interrogation platform; and
step c) further includes inserting said card into operable position in association with said interrogation platform.

* * * * *